United States Patent [19]

Schwabe et al.

[11] Patent Number: 4,695,322

[45] Date of Patent: Sep. 22, 1987

[54] DUST-FREE ALGINATE IMPRESSION MATERIALS

[75] Inventors: Peter Schwabe; Reiner Voigt, both of Leverkusen, Fed. Rep. of Germany

[73] Assignee: Bayer Aktiengesellschaft, Leverkusen, Fed. Rep. of Germany

[21] Appl. No.: 913,824

[22] Filed: Sep. 29, 1986

[30] Foreign Application Priority Data

Oct. 2, 1985 [DE] Fed. Rep. of Germany ....... 3535132

[51] Int. Cl.$^4$ ........................... A61K 6/10; A61C 9/00
[52] U.S. Cl. .................................. 106/35; 106/38.23; 106/205; 106/209; 252/88; 252/383; 252/384
[58] Field of Search ...................... 106/35, 38.23, 205, 106/209; 252/88, 383, 384

[56] References Cited

U.S. PATENT DOCUMENTS

| | | | |
|---|---|---|---|
| 2,345,255 | 3/1944 | Gross | 106/209 |
| 4,394,172 | 7/1983 | Scheuble et al. | 106/35 |
| 4,543,372 | 9/1985 | Watanabe et al. | 106/35 |

FOREIGN PATENT DOCUMENTS 3424146  1/1986  Fed. Rep. of Germany ........ 106/35

*Primary Examiner*—Robert A. Wax
*Attorney, Agent, or Firm*—Sprung Horn Kramer & Woods

[57] ABSTRACT

In the making of an impression wherein an impression material comprising an alginate, a pulverulent material and a dust-reducing coating is mixed with water to form a paste, the paste is positioned about a mold member, and permitted to harden, the improvement wherein such coating comprises an iso-paraffin. There is reduced dusting.

8 Claims, No Drawings

DUST-FREE ALGINATE IMPRESSION MATERIALS

The invention relates to impression materials based on alginate, their preparation and their use for the production of impressions, preferably in the dental field.

In the production of inlays, crowns, bridges and prostheses in the dental field, a negative of the region in question is produced with the aid of impression materials, and is then filled by pouring in modelling gypsum. The desired adjustments can then be made with the aid of the gypsum model.

Impression materials consisting of alginates have been used for a long time to produce impressions in the dental field (U.S. Pat. No. 2,345,255). To prevent dusting of the powder, the alginate powder is coated with particular polymers, such as polypropylene glycol (U.S. Pat. No. 4,394,172).

Molding materials consisting of alginates, gelling agents, regulators, fillers, surface-active agents and hydrocarbons are known from Japanese Patent No. 59/225,104. Squalane, squalene, nonane, decane, undecane, dodecane and tridecane are mentioned as hydrocarbons.

However, the known molding materials based on alginates still form dust and are not completely satisfactory.

An impression material based on alginates has been found, which is characterized in that the pulverulent material is coated with iso-paraffin.

The molding materials according to the invention do not form dust.

Iso-paraffins of the formula

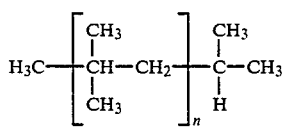

in which n represents 2, 3, 4 or 5, are preferred for the impression materials according to the invention.

Iso-paraffins in which n represents 3 or 4 are particularly preferred.

It is of course possible to use mixtures of isoparaffins. 2,2,4,4,6,6,8-heptamethyl-nonane and 2,2,4,4,6,6,8,8,10-nonamethyl-undecane are particularly preferred.

The iso-paraffins are obtained in a manner which is known per se by catalytic oligomerization of isobutene with subsequent hydrogenation (CAS No. 27 235-48-9).

The iso-paraffins have a viscosity in the range from 4 to 8 mPa.s/20° C. and a boiling point in the range from 210° to 3200° C. The flame point is in the range from 90° to 130° C. and the ignition point is in the range from 375° to 420° C.

Preferably, the impression materials according to the invention contain 0.5 to 7% by weight, in particular 2.5 to 5% by weight, of iso-paraffin.

The impression materials according to the invention in general contain a soluble alginate (for example the sodium and/or potassium salt of alginic acid in an amount of preferably 8 to 25% by weight, in particular 10 to 17% by weight, a metal compound which forms a water-insoluble salt with alginic acid (for example lead, calcium or magnesium compounds, such as magnesium oxide, magnesium carbonate or calcium sulphate) in an amount of preferably 5 to 40% by weight, in particular 10 to 25% by weight, an agent which retards hardening (for example an alkali metal phosphate, diphosphate or polyphosphate) in an amount of preferably 0.5 to 10% by weight, in particular 1 to 5% by weight, and fillers (for example gypsum, kieselguhr, diatomaceous earth, clay, talc and the like) in an amount of preferably 25 to 85% by weight, in particular 40 to 75% by weight. If appropriate, the impression material can contain other additives, such as, for example, dyestuffs and flavoring agents and compounds which improve the compatibility with gypsum (for example potassium fluorotitanate or potassium fluorozirconate).

The impression materials according to the invention are prepared by adding the iso-paraffin to the pulverulent mixture of the abovementioned components, preferably at the room temperature of the mixture. However, it is also possible to treat only one or some of the components with iso-paraffin and then to add the remaining components. The iso-paraffin is advantageously added in a paddle mixer, for example a Lödige mixer, the walls of which are provided with jets through which the iso-paraffin is sprayed onto the pulverulent mixture.

The impression materials according to the invention are distinguished by a greater sharpness of contour and a more rapid dispersibility in water. They are pliable and can easily be detached from the teeth after hardening.

EXAMPLES

An alginate impression material was prepared by mixing the following components:

| | |
|---|---|
| potassium alginate | 15.0% |
| CaSO$_4$.2H$_2$O | 10.6% |
| MgCO$_3$ | 1.5% |
| Na$_4$P$_2$O$_7$ | 1.5% |
| K$_2$TiF$_6$ | 3.4% |
| Kaolin | 10.0% |
| Talc | 2.1% |
| Diatomaceous earth | 55.9% |

The pulverulent material was divided into several portions, which were treated with various coating agents in the following manner: the mixture was introduced into a powder mixer (Plough mixer of 3 l volume) and sprayed with the particular coating agent from above by means of a spray gun. The stirrer was switched off after 10 minutes.

The samples thus coated were tested for their relative formation of dust. The apparatus used for this is a chamber of dimensions 50×50×50 cm, which has an inlet nozzle and a suction device with a membrane filter. The pump on the suction device is switched on and set at a flow rate of 27/minute. 400 mg of sample are blown into the chamber by a blast of compressed air via a sample funnel attached to the inlet nozzle, and the pump is switched off 4 minutes later. The weight of the dust deposited on the membrane filter multiplied by the empirical factor of 9.4 gives the average dust concentration in the chamber.

The results (dust concentration in mg/m$^3$) are summarized in the following table (mean values from 5 measurements):

| % by weight of coating agent | A | B | C | D | E |
|---|---|---|---|---|---|
| 1 | | | | 263 | 376 |
| 2 | 225 | 291 | | 235 | 328 |
| 3 | 206 | 272 | 228 | 216 | 244 |
| 4 | 169 | 235 | 222 | 197 | |
| 5 | 152 | 197 | 179 | 178 | |

A ... 2,2,4,4,6,6,8,8,10-nonamethyl-undecane
B ... 2,2,4,4,6,6,8-heptamethyl-nonane
C ... polydimethylsiloxane (100 cP/20° C.) (for comparison)
D ... paraffin oil of 180 cP/23° C. (for comparison)
E ... polyethylene glycol (for comparison)

Samples coated with substance C could not be stirred into water.

It will be understood that the specification and examples are illustrative but not limitative of the present invention and that other embodiments within the spirit and scope of the invention will suggest themselves to those skilled in the art.

We claim:

1. In an impression material comprising an alginate, a pulverulent material and a dust-reducing coating, the improvement wherein such coating comprises an iso-paraffin.

2. An impression material according to claim 1, wherein the iso-paraffin is of the formula

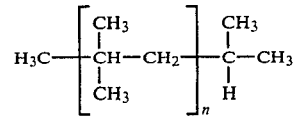

in which
n is 2, 3, 4 or 5.

3. An impression material according to claim 1, wherein the iso-paraffin comprises at least one of 2, 2, 4, 4, 6, 6, 8-heptamethyl-nonane and 2, 2, 4, 4, 6, 6, 8, 8,10-nonamethylundecane.

4. An impression material according to claim 1, wherein the iso-paraffin is prepared by catalytic oligomerization of isobutene with subsequent hydrogenation.

5. An impression material according to claim 1, containing about 0.5 to 7% by weight of the iso-paraffin.

6. An impression material according to claim 1, containing about 2.5 to 5% by weight of the iso-paraffin.

7. An impression material according to claim 1, further containing a gelling agent, retarding agent, filler and adjuvant.

8. In the making of an impression wherein an impression material comprising an alginate, a pulverulent material and a dust-reducing coating is mixed with water to form a paste, the paste is positioned about a mold member, and permitted to harden, the improvement wherein such coating comprises an iso-paraffin.

* * * * *

UNITED STATES PATENT AND TRADEMARK OFFICE
CERTIFICATE OF CORRECTION

PATENT NO. : 4,695,322
DATED : Sept. 22, 1987
INVENTOR(S) : Schwabe et al.

It is certified that error appears in the above-identified patent and that said Letters Patent is hereby corrected as shown below:

Col. 1, line 55                      Delete "3200°C" and substitute --320°C--

Col. 2, line 58                      Delete "27/minute" and substitute --27 1/minute--

Signed and Sealed this

Tenth Day of May, 1988

Attest:

DONALD J. QUIGG

Attesting Officer            Commissioner of Patents and Trademarks